(12) United States Patent
Pfeiffer et al.

(10) Patent No.: US 8,257,273 B2
(45) Date of Patent: Sep. 4, 2012

(54) DEVICE FOR DETERMINING CARDIOPULMONARY VOLUMES AND FLOWS OF A LIVING BEING

(75) Inventors: Ulrich J. Pfeiffer, Munich (DE); Reinhold Knoll, Munich (DE); Frédéric Michard, Bièvres (FR)

(73) Assignee: Pulsion Medical Systems SE, Feldkirchen (DE)

( * ) Notice: Subject to any disclaimer, the term of this patent is extended or adjusted under 35 U.S.C. 154(b) by 1179 days.

(21) Appl. No.: 11/884,318

(22) PCT Filed: Jan. 3, 2006

(86) PCT No.: PCT/EP2006/050006
§ 371 (c)(1),
(2), (4) Date: Nov. 14, 2007

(87) PCT Pub. No.: WO2006/087245
PCT Pub. Date: Aug. 24, 2006

(65) Prior Publication Data
US 2008/0146945 A1    Jun. 19, 2008

(30) Foreign Application Priority Data
Feb. 18, 2005   (DE) .................. 10 2005 007 592

(51) Int. Cl.
*A61B 5/02* (2006.01)

(52) U.S. Cl. .................. 600/526; 600/484; 600/505

(58) Field of Classification Search .......... 600/481–507, 600/526
See application file for complete search history.

(56) References Cited

U.S. PATENT DOCUMENTS 5,135,000 A * 8/1992 Akselrod et al. ............. 600/458
(Continued)

FOREIGN PATENT DOCUMENTS
EP    1 236 435 A1    9/2002
(Continued)

OTHER PUBLICATIONS

Cutler et al., "A Thermodilution Method for Quantification of Bidirectional Shunts," 1979, Computers and Biomedical Research 12, 379-410.*

(Continued)

*Primary Examiner* — Patricia Mallari
*Assistant Examiner* — Eric Messersmith
(74) *Attorney, Agent, or Firm* — Collard & Roe, P.C.

(57) ABSTRACT

The invention relates to a device for determining cardiopulmonary volumes and flows of a living being. According to the invention, the evaluation unit (14) of a transpulmonary measurement arrangement, preferably having a central-vein catheter and an arterial catheter (11, 12), is set up, in terms of program technology, for the purpose of taking a possible short-circuit current from the right to the left half of the heart (RL shunt) and/or from the left to the right half of the heart (LR shunt) of the living being into consideration, without the use of a right-heart catheter being required in this connection, or any recourse to pulmonary artery measurement values having to take place at all. In this connection, a model is used as the basis, which contains the function y (system response) corresponding to a dilution curve as the convolution of a disruption function I with several terms that contain characteristic times as model parameters. The terms correspond to ideally mixed volumes or delay elements that are assumed as simplifications for the right atrium (RA), the right ventricle (RV), the pulmonary blood volume (PBV), the extravasal thermal volume (ETV), the left atrium (LA), and the left ventricle (LV).

18 Claims, 4 Drawing Sheets

U.S. PATENT DOCUMENTS

Figure 1:
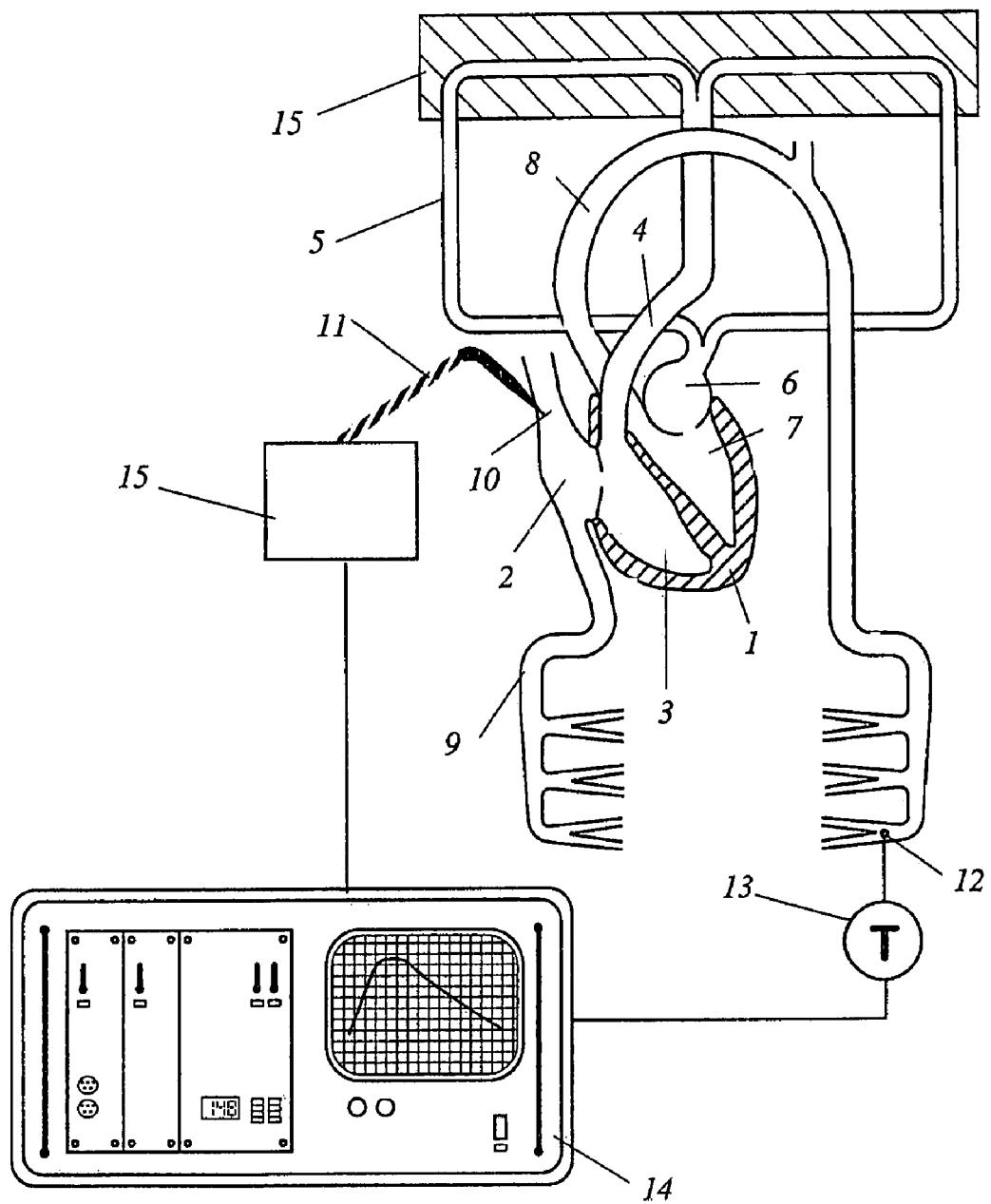

| | | | | |
|---|---|---|---|---|
| 5,526,817 | A | * | 6/1996 | Pfeiffer et al. ............... 600/504 |
| 5,595,181 | A | * | 1/1997 | Hubbard ...................... 600/505 |
| 6,470,889 | B1 | * | 10/2002 | Bae et al. ...................... 604/28 |
| 6,672,172 | B2 | * | 1/2004 | Tulkki et al. ............... 73/861.05 |

FOREIGN PATENT DOCUMENTS

| | | | |
|---|---|---|---|
| WO | WO/93/21823 | | 11/1993 |
| WO | WO 97/48334 | * | 12/1997 |
| WO | WO9748334 | * | 12/1997 |
| WO | WO/01/30237 | | 5/2001 |

OTHER PUBLICATIONS

Michard and Perel, "Management of ciculatory and respiratory failure using less invasive columetric and functional hemodynamic monitoring." 2003, Yearbook of Intensive Care and Emergency Medicine, 508-520.*

Pearl and Siegel, "Thermodilution Cardiac Output Measurement with a Large Left-to-Right Shunt," Apr. 1991, Journal of Clinical Monitoring, vol. 7, No. 2, 146153.*

Cutler C A Et. Al.: "A Thermodilution Method for Quantification of Bidirectional Shunts" *Computers and Biomedical Research, An Internal Journal.* Aug. 1979, vol. 12, No. 4, pp. 379-410—p. 383, Fig. 2.

Wietasch, J.K. Götz, "Die Doppelindikatordilution zur Quantifizierung von Herzzeitvolumen und Links-Techts-Shunt bei Patienten mit Kongenitalem Vitium cordis" Göttingen 1995 and English translation of relevant parts (20 pages).

Sonoda, Y. Et al. *"Signal Separation from Superposed Waves—Application to the Indicator-Dilution-Curve"* Research paper magazine D-2, vol. 75 (1992), No. 2, S. 410-413, Institute of Electronics, Information and Communication Engineers (attached with translation of relevant portions).

* cited by examiner

DEVICE FOR DETERMINING CARDIOPULMONARY VOLUMES AND FLOWS OF A LIVING BEING

CROSS REFERENCE TO RELATED APPLICATIONS

Applicants claim priority under 35 U.S.C. §119 of German Application No. 10 2005 007 592.4 filed Feb. 18, 2005. Applicants also claim priority under 35 U.S.C. §365 of PCT/EP2006/050006 filed Jan. 3, 2006. The international application under PCT article 21(2) was not published in English.

The present invention relates to a device for determining at least one hemodynamic parameter of a living being, particularly a device for determining cardiopulmonary volumes and flows of a living being.

Devices for determining hemodynamic parameters from a dilution curve obtained by means of invasive measurements are in broad use, particularly in intensive-care medicine. In this connection, the hemodynamic parameters are, in particular, characteristic volumes or volume flows, such as the cardiac output (CO), the global end-diastolic volume (GEDV), and the volume of the extravasal lung water (EVLW). Corresponding systems are commercially available and usually work with cold (i.e. a cooled bolus) as the indicator. In addition to the right-heart catheter systems that are widespread, with which thermodilution measurements are carried out with the pulmonary artery as the measurement site, systems for transpulmonary thermodilution measurement have established themselves on the market.

Methods and devices for transpulmonary thermodilution measurement have been disclosed in WO 93/21823 A1 and WO 01/30237 A1, among others, as well as the literature cited in them.

In the determination of hemodynamic parameters on the basis of measured dilution curves, inaccuracies or errors can occur on the basis of patient-specific anomalies. Such anomalies include short-circuit disruption functions of the right atrium to the left atrium (so-called right-left shunt, RL shunt), or from the left ventricle to the right ventricle (so-called left-right shunt, LR shunt).

The determination of a left-right shunt within the framework of a thermodilution measurement with a right-heart catheter is disclosed in U.S. Pat. No. 5,595,181. In this connection, the shunt determination takes place by means of a comparison of the temperature progression over time with an assumed temperature progression without shunt. Since a temperature progression without shunt is necessarily unknown for the same individual under identical conditions, this is merely an estimate of rather low accuracy. The use of a right-heart catheter in the form of a conventional balloon catheter furthermore bears a not insignificant medical risk, since here, the heart itself is fundamentally the object of an invasive measure. Furthermore, the defect of a right-left shunt, which occurs significantly more frequently, is not taken into consideration.

In the dissertation by J. K. G. Wietach, "*Die Doppelindikatordilution zur Quantifizierung von Herzzeitvolumen und Links-Rechts-Shunt bei Patienten mit kongenitalem Vitium cordis*" [Dual-indicator dilution for quantification of cardiac output and left-right shunt in patients suffering from congenital vitium cordis], Göttingen 1995, the determination of a left-right shunt by means of the dual-indicator dilution technique is described, i.e. by means of parallel determination of dilution curves by means of pulmonary artery measurement and aorta measurement. Here, too, the application of a right-heart catheter is required for the pulmonary artery measurement, with the attendant medical risks.

With this background, it is the task of the invention to create a device for determining hemodynamic parameters of a living being, which guarantee reliable hemodynamic monitoring, which is as gentle on the patient as possible and subject to little error, even in the case of patients having heart defects that cause short-circuit currents.

This task is accomplished according to one aspect of the present invention, with a device disclosed herein.

Advantageous embodiments of the invention can be configured according to further embodiments disclosed herein.

In surprising manner, even for a person skilled in the art, a suitable program technology set-up of the evaluation unit of a transpulmonary measurement arrangement, preferably having a central-vein catheter and an arterial catheter, is sufficient to take a possible short-circuit current from the right to the left half of the heart (RL shunt) and/or from the left to the right half of the heart (LR shunt) into consideration, without the use of a right-heart catheter being required for this, or recourse to pulmonary artery measurement values having to take place at all.

In this connection, a model is preferably used as the basis, in which the function y that corresponds to the dilution curve is included as a convolution of the disruption function I with several terms that contain characteristic times as model parameters. The terms correspond to ideally mixed volumes or delay elements that are stated as simplifications for the right atrium RA, the right ventricle RV, the pulmonary blood volume PBV, the extravasal thermal volume ETV, the left atrium LA, and the left ventricle LV.

The shunt can be in both directions as well as intracardial and extracardial.

Preferably, the evaluation unit is set up, in terms of program technology, to carry out the following steps: (a) estimating a starting point and a dilution peak of the dilution curve y, (b) calculating a mean transit time $MTT = \int y \cdot t \, dt / \int y \, dt$ (with time variable t) and a decay time DST (from the exponential decay of the dilution curve y according to $y \propto \exp(-t/DST)$ after the dilution peak, (c) determining model parameters of the underlying model, using the mean transit time MTT and the decay time DST, (e) calculating the cardiac output CO and a short-circuit current ratio s, (f) calculating the terms that contain the model parameters, and (g) calculating the hemodynamic parameter.

The determination of the model parameters can advantageously take place by means of the partial steps (i) adapting a model curve to the dilution curve (for example by means of a Levenberg-Marquardt algorithm) and (ii) determining the model parameters from the model curve.

Alternatively, the model parameters can also be advantageously determined by means of the following partial steps: (i) determining a short-circuit peak that lies ahead of the dilution peak, (ii) determining a tangent to the dilution peak below the short-circuit peak, which encloses the greatest possible area with the dilution curve, and (iii) estimating the model parameters using curve parameters that can be determined from the location of the starting point of the dilution curve, the contact points of the tangent, the short-circuit peak, and the dilution peak.

Even though a central-vein catheter and an arterial catheter unit are provided according to a preferred embodiment, alternative embodiments of the invention can also be advantageous, in which the arterial signal is detected in non-invasive manner, for example by way of a tympanometric temperature measurement site or by means of optical methods, and/or the system disruption is triggered not in the central vein but rather in peripheral manner. In the last case mentioned, it merely needs to be known or possible to estimate with a sufficient approximation what additional delay as the result of the peripheral triggering must be taken into consideration.

Fundamentally, the disruption can take place by means of the introduction of heat, "introduction of cold" (injection of a cooled bolus), lithium chloride injection (LiCl), indocyanine green injection (ICG), or other indicators.

The disruption function can fundamentally have any desired progression (but one known with sufficient accuracy); for example, a pseudo-stochastic distribution is also possible.

Fundamentally, any variant of the invention described or indicated within the framework of the present application can be particularly advantageous, depending on the economic and technical conditions in an individual case. Unless something is stated to the contrary, and to the extent that this is fundamentally possible in technical terms, individual characteristics of the embodiments described are interchangeable or can be combined with one another.

Figure 2:
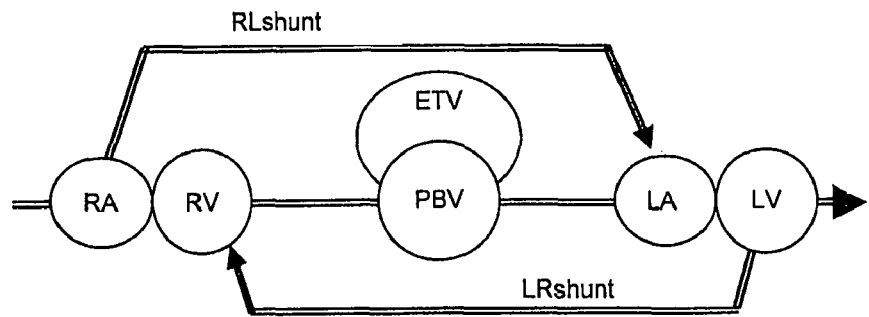
Figure 3:
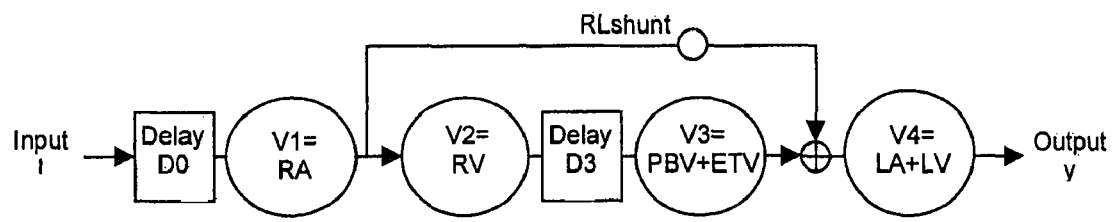
Figure 4:
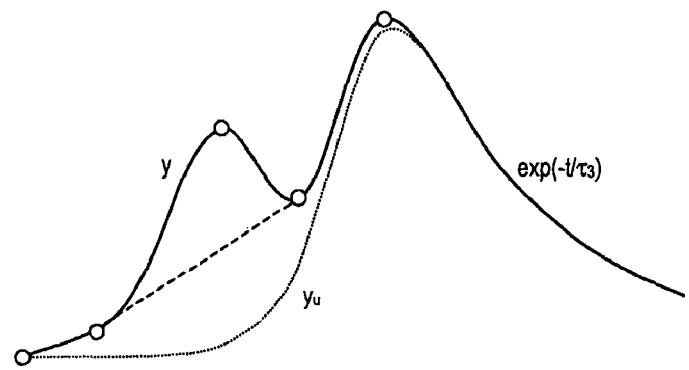
Figure 5:
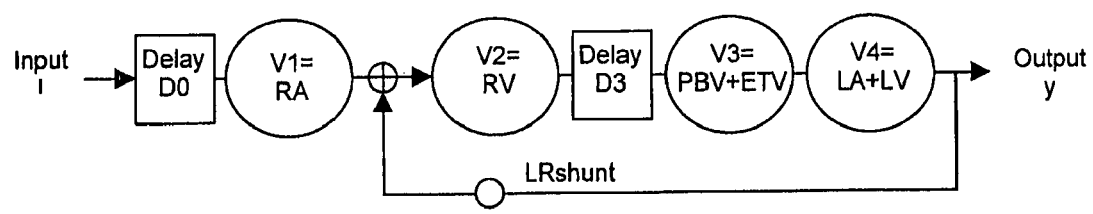
Figure 6:
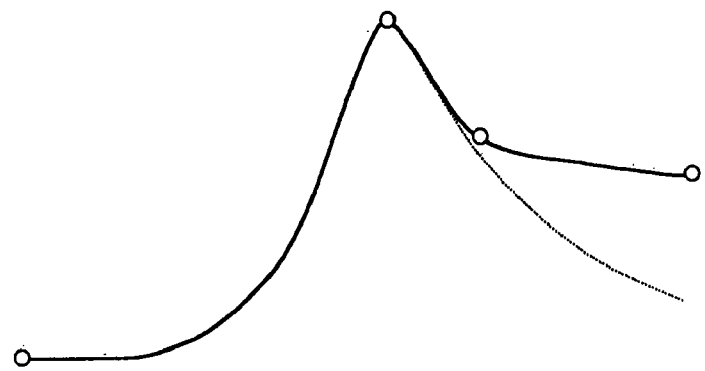
Figure 7:
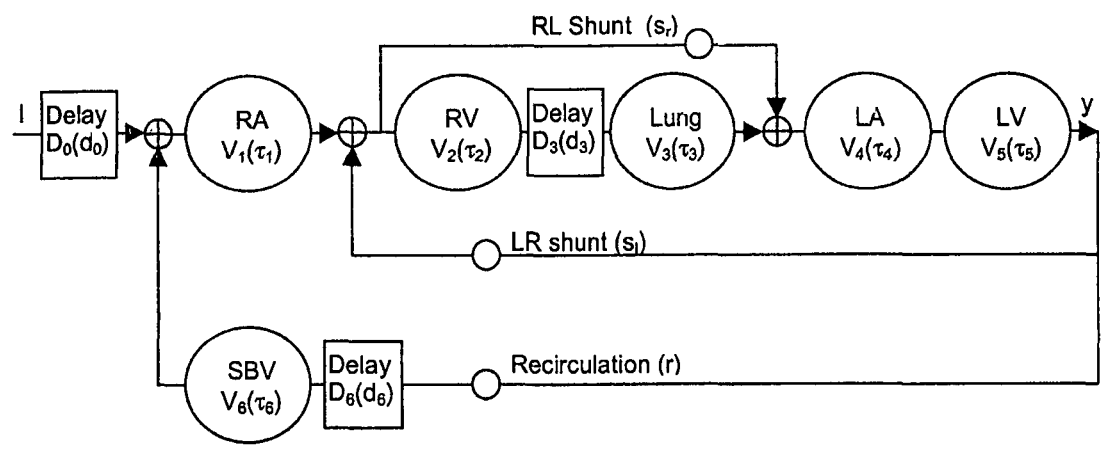

In the following, examples of preferred embodiments of the present invention will be explained in greater detail, using the related drawings. In this connection, the drawings are to be understood as being purely schematic. They show:

FIG. 1 a schematic, sketch-like representation of a cardiovascular system, with the disposition of essential components of a device according to the invention, FIG. 2 a circuit schematic type illustration of possible short-circuit currents, FIG. 3 a circuit schematic type sketch for taking into consideration a right-left shunt according to a model that can be used as a basis according to the invention, FIG. 4 a sketch-like representation of a dilution curve y(t) with a peak that is attributable to right-left shunt ahead of the dilution peak, FIG. 5 a circuit schematic type sketch for taking into consideration a left-right shunt according to a model that can be used as a basis according to the invention, FIG. 6 a sketch-like representation of a dilution curve y(t) with a flattening that is attributable to left-right shunt behind the dilution peak, FIG. 7 a circuit schematic type sketch for taking into consideration left-right shunt, right-left shunt, and recirculation according to a model that can be used as a basis according to the invention.

The device shown in FIG. 1 has a central vein catheter 11, which permits the injection of a cooled bolus into the upper vena cava 10 of the patient. In order to be able to indicate the evaluation of the underlying disruption function as accurately as possible, as precise as possible an adherence to the predetermined injectate temperature, injectate amount, and injection duration (to be selected to be as short as possible), i.e. detection of the same is recommended. This can also take place in automated manner by means of a suitable metering pump 15 integrated into the evaluation unit 14. Likewise, however, a bolus injection applied manually is also possible.

An arterial catheter 12 (indicated in FIG. 1 only by marking the measurement site), which has a temperature sensor 13 connected with the evaluation unit 14, serves to detect a time-dependent temperature signal, from which a thermodilution curve y is obtained and processed further, as a system response, in the evaluation unit 14, which is appropriately equipped in terms of program technology.

The cold indicator moves from the injection site 10 to the measurement site 12, passing through the right atrium 2 and the left ventricle 3 of the heart 1, through the pulmonary circulation 5 by way of the pulmonary artery 4, with extravasal thermal volume (ETV, approximately equivalent to extravasal lung water volume EVLW) 15, through the left atrium 6, the left ventricle 7, and the aorta 8.

In place of the application of a cold indicator, other methods, which are actually known, for introducing a disruption in the circulation can also be advantageously used. For example, a heat pulse can be introduced by way of the central vein catheter 11, for which purpose the latter can be equipped with suitable heating agents. Furthermore, the injection of an optically detectable indicator is also possible, whereby the arterial catheter 12 can be equipped with a fiber-optic sensor for the concentration measurement, in order to determine the system response.

Using FIG. 2, the short-circuit currents that might possibly occur in the heart 1 are illustrated once again: If right-left shunt (RLshunt) occurs between the right atrium RA and the left atrium LA, part of the blood does not flow through the pulmonary circulation 5 (made clear in FIG. 2 by means of the pulmonary blood volume PBV with the extravasal thermal volume ETV that must also be taken into consideration), and is therefore not oxygenated, and this is of significance in further diagnostic considerations. If left-right shunt (LR-shunt) occurs between the left ventricle LV and the right ventricle RV, part of the oxygenated blood does not flow into the body circulation 9 and should therefore not be attributed to the cardiac output CO.

Taking at least one of these possible short-circuit currents into account in calculating the cardiac output and/or other hemodynamic parameters is implemented in the program technology set-up of the evaluation unit 14, according to the invention.

FIG. 3 illustrates a model that is suitable for the program technology set-up of the evaluation unit 14 for taking the right-left shunt into consideration in calculating hemodynamic volumes. A serial circuit of right atrium RA, right ventricle RV, pulmonary blood volume PBV (with extravasal thermal volume ETV also to be taken into consideration), and totality of left atrium LA and left ventricle LV is considered. The right-left shunt is connected in parallel to the right ventricle RV and pulmonary blood volume PBV (cf. FIG. 2).

A first ideally mixed volume V1 with a characteristic time $\tau_1$ is assumed for the right atrium RA, another ideally mixed volume V2 with a characteristic time $\tau_2$ is assumed for the right ventricle, a third ideally mixed volume V3 with a characteristic time $\tau_3$ and a delay element ("delay") D3 is assumed for the totality of the pulmonary blood volume PBV and extravasal thermal volume ETV, and a fourth ideally mixed volume V4 with a characteristic time $\tau_4$ is assumed for the totality of the left atrium LA and left ventricle LV. The characteristic times $\tau_n$ are defined as the quotient of the corresponding volume Vn and the volume flow Qn through this volume.

Since a linear delay in the right and left half of the heart has an equivalent effect on the system response ("output") y, corresponding effects are combined in the delay element ("delay") D0. The delay element D0 can be taken into consideration by means of selecting a corrected starting time.

For the system response ("output") y, the following applies:

$$y = I * D0 * V1 * (s \cdot \delta + (1-s) \cdot V2 * D3 * V3) * V4$$

with convolution operator $*$, input function ("input") or disruption function I, Dirac function $\delta$, shunt ratio (ratio of shunt to cardiac output) s:=RLshunt/CO.

The measured dilution curve y, the typical progression of which, when a right-left shunt occurs, is sketched in FIG. 4, can be broken down into two parts. The liquid elements of the blood that pass through the lung circulation 5 are described by a theoretical curve $y_u$ that is free of short circuits. The other liquid elements, which are attributable to the shunt, are described by a theoretical shunt curve $$y_s = y - y_u$$

The shunt ratio s=RLshunt/CO corresponds to the quotient of the integral above the shunt curve $y_s$ and the integral above the measured curve y.

The disruption function I is considered to be a Dirac delta function with an ideally short injection time and indicator amount m, according to $$I(m/CO) \cdot \delta(t) = co \cdot \delta(t)$$

The following applies for the time constant:

$$\tau_1 = V1/CO$$

$$\tau_2 = V2/((1-s) \cdot CO)$$

$$\tau_3 = V3/((1-s) \cdot CO)$$

$$\tau_4 = V4/CO$$

and
from this, the following is obtained:

$$y(t) = \frac{c_0 \cdot s}{\tau_1 - \tau_4}\left[\exp\left(\frac{-t+d_0}{\tau_1}\right) - \exp\left(\frac{-t+d_0}{\tau_4}\right)\right] \cdot \delta(t - d_0) + y_u(t)$$

$$y_u(t) = \frac{c_0 \cdot (1-s)}{(\tau_1 - \tau_4)(\tau_2 - \tau_3)}\left[\left(\frac{\tau_2 \tau_1}{\tau_2 - \tau_1} - \frac{\tau_2 \tau_4}{\tau_2 - \tau_4}\right)\exp\left(\frac{-t+d_0+d_3}{\tau_2}\right) - \right.$$
$$\left(\frac{\tau_3 \tau_1}{\tau_3 - \tau_1} - \frac{\tau_3 \tau_4}{\tau_3 - \tau_4}\right)\exp\left(\frac{-t+d_0+d_3}{\tau_3}\right) -$$
$$\left(\frac{\tau_2 \tau_1}{\tau_2 - \tau_1} - \frac{\tau_3 \tau_1}{\tau_3 - \tau_1}\right)\exp\left(\frac{-t+d_0+d_3}{\tau_1}\right) +$$
$$\left.\left(\frac{\tau_2 \tau_4}{\tau_2 - \tau_4} - \frac{\tau_3 \tau_4}{\tau_3 - \tau_4}\right)\exp\left(\frac{-t+d_0+d_3}{\tau_4}\right)\right] \cdot \sigma(t - d_0 - d_3)$$

In this, do and d3 designate the characteristic times that correspond to the delay elements D0 and D3, respectively. The initial concentration $c_o$ can be determined by means of integration of the dilution curve:

$$co = \int y \, dt.$$

For the greatest volume V3, the characteristic time $\tau_3$ of the time constant DST (down slope time) of the exponential decay y∝exp(-t/DST) is equated with the dilution curve y after the dilution peak, according to $$\tau_3 = DST.$$

The mean transit time MTT that can be determined from the dilution curve according to $$MTT = \int y \cdot t \, dt / \int y \, dt$$

is equal to the sum of the characteristic times $\tau_1, \tau_2, \tau_3, D3, \tau_4$, so that $$\tau_3 = MTT - DST - \tau_1 - \tau_2 - d3.$$

For the right and left atrium as well as the right and left ventricle, simplifying constant volume conditions can be assumed, for example $$\tau_1 = 0.6 \cdot \tau_2$$

and $$\tau_4 = 1.3 \cdot \tau_2.$$

The remaining model parameters s, $d_o$ and d3 can preferably be determined by means of a curve adaptation algorithm (for example the Levenberg-Marquardt algorithm).

By means of the model parameters determined according to the above equations, the evaluation unit 14 can calculate various hemodynamic parameters with lesser error deviations than is possible according to the state of the art:

Cardiac output:

$$CO = m/co$$

Pulmonary thermal volume:

$$PTV = V3 = \tau_3 \cdot (1-s) \cdot CO$$

Intrathoracic thermal volume:

$$ITTV = V1 + V2 + V3 + V4 = (\tau_1 + \tau_4) \cdot CO + (\tau_2 + \tau_3) \cdot (1-s) \cdot CO$$

Global end-diastolic volume:

$$GEDV = V1 + V2 + V4 = (\tau_1 + \tau_4) \cdot CO + \tau_2 \cdot (1-s) \cdot CO$$

Intrathoracic blood volume:

$$ITBV = a \cdot GEDV + b = a \cdot ((\tau_1 + \tau_4) \cdot CO + \tau_2 \cdot (1-s) \cdot CO) + b$$

Extravasal lung water:

$$EVLW = ITTV - ITBV = (\tau_1 + \tau_4) \cdot CO + (\tau_2 + \tau_3) \cdot (1-s) \cdot CO - a \cdot ((\tau_1 + \tau_4) \cdot CO + \tau_2 \cdot (1-s) \cdot CO) + b$$

Cardiac function index:

$$CFI = CO/GEDV = 1/(\tau_1 + \tau_4 + \tau_2 \cdot (1-s))$$

It is advantageous if the calculation operations are implemented in the program technology set-up of the evaluation unit 14 as follows. After estimating the starting point of the dilution curve y and the dilution peak with suitable criteria, which can be based on the state of the art, the mean transit time MTT and the decay time DST are calculated. The model function is adapted to the dilution curve determined by means of measurement technology by means of a suitable algorithm, with the least possible deviation. The cardiac output Co and the shunt ratio s are calculated with the model parameters from the adapted model function. Subsequently, the model volumes and other hemodynamic parameters can be calculated.

If the processor resources of the evaluation unit 14 are limited, it is advantageous that the calculation operations can also be implemented alternatively, essentially as follows, in the program technology set-up of the evaluation unit 14. After estimating the starting point of the dilution curve y and the dilution peak with suitable criteria, which can be based on the state of the art, the mean transit time MTT and the decay time DST are calculated. A shunt peak that lies ahead of the thermodilution peak is determined (see FIG. 4), as is a tangent (broken line in FIG. 4) to the dilution curve y below the short-circuit peak, which encloses the greatest possible area with the dilution curve y. The characteristic model parameters are derived from characteristic curve parameters, for example the starting point, the maximum of the dilution peak, the maximum of the shunt peak, the contact points of the tangent of the area under the dilution curve y, and the area under the dilution curve y and the tangent. The short-circuit-free curve $y_u$ lies under the tangent. The area between tangent and dilution curve y divided by the area under the dilution curve results in a lower approximation value for the right-left shunt. Further corrections and model parameters can be determined by means of regression or solving of the model equations. The cardiac output CO and the shunt ratio s are calculated with the model parameters. Subsequently, the model volumes and other hemodynamic parameters can be calculated.

Usually, an additional peak ahead of the dilution peak can always be considered to be a right-left shunt. In an extreme case, a right-left shunt peak can be as much as about 150% higher than the dilution peak.

A premature end of exponential decay, as sketched in FIG. 6, after the dilution peak, can be assumed to be a left-right shunt. In this connection, attention must be paid to differentiating the left-right shunt from a normal re-circulation through the body circulation 9, which usually occurs under 30% of the dilution peak.

In order to take the left-right shunt into consideration, it is advantageous that fundamentally, similar calculation operations can be implemented in the evaluation unit 14 as for the determination of the right-left shunt. As illustrated in FIG. 5, again a serial circuit of right atrium RA, right ventricle RV, pulmonary blood volume PBV (with extravasal thermal volume ETV also to be taken into consideration) and the totality of left atrium LA and left ventricle LV is being considered. The left-right shunt, in the reverse flow direction, is connected in parallel to the right ventricle RV, pulmonary blood volume PBV and the totality of the left atrium LA and left ventricle LV. For simplification, several small volumes can be simulated with a common volume with time delay.

A first ideally mixed volume V1 with a characteristic time $\tau_1$ is assumed for the right atrium RA, another ideally mixed volume V2 with a characteristic time $\tau_2$ is assumed for the right ventricle, a third ideally mixed volume V3 with a characteristic time $\tau_3$ and a delay element ("delay") D3 is assumed for the totality of the pulmonary blood volume PBV and extravasal thermal volume ETV, and a fourth ideally mixed volume V4 with a characteristic time $\tau_4$ is assumed for the totality of the left atrium LA and left ventricle LV. The characteristic times $\tau_n$ are defined as the quotient of the corresponding volume Vn and the volume flow Qn through this volume.

Since a linear delay in the right and left half of the heart has an equivalent effect on the system response ("output") y, corresponding effects are combined in the delay element ("delay") D0. The delay element D0 can be taken into consideration by means of selecting a corrected starting time.

For the system response ("output") y, the following applies:

$$y=(I*D0*V1+y \cdot \text{LRshunt} \cdot \delta)*V2*D3*V3*V4$$

with convolution operator *, input function ("input") or disruption function I, Dirac function $\delta$ and left-right shunt LRshunt.

In a first approximation, the disruption or input function ("input") I can be considered to be a Dirac delta function $\delta$, i.e. having a disappearing duration. Usually, however, an injection lasts about two seconds. In the shunt calculation, this can lead to a significant error. Alternatively to this, therefore, there is the possibility, according to the invention, of assuming a constant flow 1/p during the injection period p, for the disruption function I, and therefore of stating the disruption function I as the different of two Heaviside step functions according to $$I=(\sigma(t)-\sigma(t-p))/p.$$

According to an advantageous further development of the invention, left-right shunt and right-left shunt can be taken into consideration simultaneously, with an expanded model and multi-dimensional curve adaptation, and furthermore, the re-circulation through the body circulation 9 can advantageously be taken into consideration. The related circuit schematic is shown in FIG. 7.

A first ideally mixed volume V1 with a characteristic time $\tau_1$ is assumed for the right atrium RA, another ideally mixed volume V2 with a characteristic time $\tau_2$ is assumed for the right ventricle, a third ideally mixed volume V3 with a characteristic time $\tau_3$ and a delay element ("delay") D3 with a characteristic time $d_3$ is assumed for the totality of the pulmonary blood volume PBV and extravasal thermal volume ETV, and a fourth ideally mixed volume V4 with a characteristic time $\tau_4$ is assumed for the left atrium LA, and a fifth ideally mixed volume V5 with a characteristic time $\tau_5$ is assumed for the left ventricle LV. The characteristic times $\tau_n$ are again defined as the quotient of the corresponding volume Vn and the volume flow Qn through this volume.

Delay components in the right and left half of the heart are again summarized effects in the delay element ("delay") D0, which can be taken into consideration by means of selecting a corrected starting time.

The left-right shunt, with shunt ratio sl, is connected in parallel, in the opposite flow direction, with the right ventricle RV, pulmonary blood volume PBV, left atrium LA, and left ventricle LV. The right-left shunt, with shunt ratio sr, is connected in parallel to the right ventricle and the pulmonary blood volume PBV. With regard to the re-circulation r, an ideally mixed volume V6 with a characteristic time $\tau_6$ for the systemic blood volume SBV and a delay element ("delay") D3 with a characteristic time da are assumed.

For the system response y, the following applies:

$$y=(I*D0+r \cdot y*D6*V6)*(V1+sl \cdot y)*(sr\delta+(1-sr) \cdot D3*V2*V3)*V4*V5$$

i.e.

$$y=(1-sr) \cdot yu+sr \cdot ysr+sl \cdot ysl+r \cdot yr$$

wherein the liquid elements of the blood that do not pass through any short circuit are described by a theoretical curve $y_u$ that is free of short circuits; the liquid elements that are attributable to the right-left shunt are described by a theoretical shunt curve $y_{sr}$, the liquid elements that are attributable to the left-right shunt are described by a theoretical shunt curve $y_{sl}$, and liquid elements that are attributable to the re-circulation are described by a theoretical curve $y_{sr}$.

The mean transit time again corresponds to the sum of the time constants of the serial circuit:

$$MTT=\tau_1+\tau_2+d3+\tau_3+\tau_4+\tau_5$$

If all the volumes of the heart are equated to Vh, and only the first re-circulation pass is taken into consideration, the following is obtained:

$$Vh=V1=V2=V4=V5$$

$$yu=(1-sr) \cdot I*D0*D3*Vh^4*V3$$

$$ysr=sr \cdot I*D0*Vh^3$$

$$ysl \approx sl \cdot (yu+ysr)*D3*Vh^3*V3$$

$$yr \approx r \cdot (yu+ysr)*D6*V6*D3*Vh4*V3$$

and finally $$y_u(t) =$$
$$(1-s)\frac{\sigma(t)-\sigma(t-p)}{p}*\left[\frac{t^3}{6\tau_h^4} \cdot \exp\left(\frac{-t}{\tau_3}\right)\right]*\left[\frac{1}{\tau_1} \cdot \exp\left(\frac{-t}{\tau_3}\right)\right]*\delta(t-d_0-d_3)$$

$$y_{sr}(t) = s\frac{\sigma(t)-\sigma(t-p)}{p}*\left[\frac{t^2}{2\tau_h^3} \cdot \exp\left(\frac{-t}{\tau_h}\right)\right]*\delta(t-d_0)$$

-continued $$y_{sl}(t) \approx s_l(y_u(t) + y_{sr}(t)) * \left[\frac{t^2}{2\tau_h^3} \cdot \exp\left(\frac{-t}{\tau_h}\right)\right] * \left[\frac{1}{\tau_3} \cdot \exp\left(\frac{-t}{\tau_3}\right)\right] * \delta(t - d_3)$$

$$y_r(t) \approx r(y_u(t) + y_{sr}(t)) * \left[\frac{1}{\tau_6} \cdot \exp\left(\frac{-t}{\tau_6}\right)\right] *$$

$$\left[\frac{t^3}{6\tau_h^4} \cdot \exp\left(\frac{-t}{\tau_h}\right)\right] * \left[\frac{1}{\tau_3} \cdot \exp\left(\frac{-t}{\tau_3}\right)\right] * \delta(t - d_3 - d_6)$$

In general, as mentioned above, non-diffusible intravasal indicators, such as LiCl or ICG, can also be used. When non-diffusible intravasal indicators are used, cardiac output (CO) and global end-diastolic volume (GEDV) can be determined, but extravasal lung water (EVLW) cannot be determined. In this connection, the algorithms can fundamentally remain unchanged as compared with the algorithms described above, with the exception that then, the greatest intrathoracic dispersion volume corresponds to the intrathoracic blood volume ITBV (in the case of LiCl or ICG indicator) instead of the intrathoracic thermal volume ITTV (in the case of cold indicator).

The invention claimed is:

1. Method of determining at least one hemodynamic parameter of a living being, which comprises:
    introducing via an extracardial effect unit into the cardiovascular system of the living being, by means of a defined effect on venous blood, a disruption that can be characterized by means of a disruption function,
    acquiring a measurement signal produced by a sensor as a function of a physical variable of arterial blood, which characterizes a system response of the cardiovascular system brought about by the disruption function, and
    calculating via an evaluation unit the hemodynamic parameter from a dilution curve y that corresponds to the time progression of the measurement signal and, in this connection, taking into consideration at least one of a possible short-circuit current from the right to the left half of the heart (RL shunt) and a possible short-circuit current from the left to the right half of the heart (LR shunt) of the living being,
    wherein a model for the cardiovascular and pulmonary circulation system of the living being is used as a basis for calculating the hemodynamic parameter, wherein the model comprises a serial circuit of several system elements and at least one system element connected in parallel for taking the short-circuit current into consideration and a program technology set-up of the evaluation unit comprises calculation operations that can be derived from a model function for a system response that corresponds to this model,
    wherein the model function comprises a mathematical convolution of terms that incorporate the system elements connected in series and the disruption function,
    wherein the terms each have a respective characteristic time as a model parameter, and
    wherein the serial circuit of several system elements is modeled as a serial circuit comprising:
    a first ideally mixed volume for the right atrium RA of the living being,
    a second ideally mixed volume for the right ventricle RV of the living being,
    a third ideally mixed volume for the totality of pulmonary blood volume PBV and extravasal thermal volume ETV of the living being and a delay element, and
    a fourth ideally mixed volume for the totality of the left atrium and the left ventricle LV of the living being assumed as system elements of the serial circuit.

2. Method according to claim 1, wherein at least one of the following variables is determined as a hemodynamic parameter:
    cardiac output CO,
    pulmonary thermal volume PTV,
    intrathoracic thermal volume ITTV,
    global end-diastolic volume GEDV,
    intrathoracic blood volume ITBV,
    extravasal lung water EVLW,
    cardiac function index CFI.

3. Method according to claim 1, wherein the a starting point of the dilution curve y is estimated and a mean transit time MTT is determined according to $$MTT = \int y \cdot t \, dt / \int y \, dt$$

with the time t
from the dilution curve y,
and wherein the mean transit time MTT is taken into consideration as the sum of the characteristic times of the first, second, third, and fourth ideally mixed volumes as well as of the delay element.

4. Method according to claim 1, wherein a dilution peak is determined, and an exponential decay time DST from an exponential drop of the dilution curve y after the dilution peak is determined according to $$y \propto \exp(-t/DST)$$

with the time t,
and wherein the exponential decay time DST is taken into consideration as a characteristic time of the third ideally mixed volume.

5. Method according to claim 1, wherein a constant ratio of the characteristic times of the first, second, and fourth ideally mixed volumes relative to one another is provided.

6. Method according to claim 1, wherein the characteristic times are determined by means of fitting, by calculations, of a model curve that corresponds to one of the model functions to the dilution curve y.

7. Method according to claim 6, wherein the fitting, by calculations, of the model curve corresponding to the model function to the dilution curve y is implemented by means of a Levenberg-Marquardt algorithm.

8. Method according to claim 1, wherein a short-circuit peak is determined as an additional peak of the dilution curve y ahead of the dilution peak, and the case of the non-existence of a short-circuit peak is provided as a condition for the non-existence of a short-circuit current from the right atrium to the left ventricle of the living being.

9. Method according to claim 8, wherein a tangent to the dilution curve y below the short-circuit peak is determined, which encloses the greatest possible area with the dilution curve y.

10. Method according to claim 1, wherein the value of the dilution curve y at the end of an exponential drop of the dilution curve y after the dilution peak is determined, and the case that the value determined exceeds a predetermined proportion of the value of the dilution curve y at the dilution peak is provided as a condition for the existence of a short-circuit current from the left ventricle to the right ventricle of the living being.

11. Method according to claim 10, wherein the predetermined proportion is at least 30 percent.

12. Method according to claim 1, wherein introducing the disruption includes bringing about a temperature change in venous blood, and the physical variable that characterizes the system response of the blood circulation is a temperature of arterial blood.

13. Method according to claim 12, wherein introducing the disruption includes giving off a temperature impulse to central-venous blood.

14. Method according to claim 12, wherein introducing the disruption in the blood circulation includes injecting a cooled bolus into venous blood.

15. Method according to claim 1, wherein introducing the disruption includes injecting an indicator into venous blood, and the physical variable that characterizes the system response of the blood circulation is an indicator concentration in arterial blood.

16. Method of determining at least one hemodynamic parameter of a living being, which comprises:
   introducing via an extracardial effect unit into the cardiovascular system of the living being, by means of a defined effect on venous blood, a disruption that can be characterized by means of a disruption function,
   acquiring a measurement signal produced by a sensor as a function of a physical variable of arterial blood, which characterizes a system response of the cardiovascular system brought about by the disruption function, and
   calculating via an evaluation unit the hemodynamic parameter from a dilution curve y that corresponds to the time progression of the measurement signal and, in this connection, taking into consideration at least one of a possible short-circuit current from the right to the left half of the heart (RL shunt) and a possible short-circuit current from the left to the right half of the heart (LR shunt) of the living being;
   wherein a Dirac function having the form $$I=co\delta(t),$$

is assumed for the disruption function, wherein $\delta$ is the Dirac delta function and co is a coefficient assumed to be a quotient of an indicator quantity m and a cardiac output CO of the living being according to co=m/CO.

17. Method of determining at least one hemodynamic parameter of a living being, which comprises:
   introducing via an extracardial effect unit into the cardiovascular system of the living being, by means of a defined effect on venous blood, a disruption that can be characterized by means of a disruption function,
   acquiring a measurement signal produced by a sensor as a function of a physical variable of arterial blood, which characterizes a system response of the cardiovascular system brought about by the disruption function, and
   calculating via an evaluation unit the hemodynamic parameter from a dilution curve y that corresponds to the time progression of the measurement signal and, in this connection, taking into consideration at least one of a possible short-circuit current from the right to the left half of the heart (RL shunt) and a possible short-circuit current from the left to the right half of the heart (LR shunt) of the living being;
   wherein a Dirac function having the form $$I=co\delta(t),$$

is assumed for the disruption function, wherein $\delta$ is the Dirac delta function and co is a coefficient determined as an integral of the dilution curve y over the time t, according to $$co=\int y\, dt.$$

18. Method of determining at least one hemodynamic parameter of a living being, which comprises:
   introducing via an extracardial effect unit into the cardiovascular system of the living being, by means of a defined effect on venous blood, a disruption that can be characterized by means of a disruption function,
   acquiring a measurement signal produced by a sensor as a function of a physical variable of arterial blood, which characterizes a system response of the cardiovascular system brought about by the disruption function, and
   calculating via an evaluation unit the hemodynamic parameter from a dilution curve y that corresponds to the time progression of the measurement signal and, in this connection, taking into consideration at least one of a possible short-circuit current from the right to the left half of the heart (RL shunt) and a possible short-circuit current from the left to the right half of the heart (LR shunt) of the living being;
   wherein the difference between two step functions is assumed for the disruption function, according to $$I=(1/p)\cdot[\sigma(t)-\sigma(t-p)],$$

wherein $\sigma$ is the Heaviside step function and p is the duration of the defined effect on central-venous blood.

* * * * *